United States Patent [19]

Serota

[11] Patent Number: 4,488,996

[45] Date of Patent: Dec. 18, 1984

[54] RAPID PRODUCTION OF ISPROPENYL ESTERS

[75] Inventor: Samuel Serota, Philadelphia, Pa.

[73] Assignee: The United States of America as represented by the Secretary of Agriculture, Washington, D.C.

[21] Appl. No.: 426,438

[22] Filed: Sep. 29, 1982

[51] Int. Cl.$^3$ .............................................. C11C 3/02
[52] U.S. Cl. ..................... 260/410.9 R; 260/410.9 N; 560/242; 560/113; 560/95
[58] Field of Search ................. 260/410.9 A, 410.9 N, 260/410.9 R; 560/242, 95, 113

[56] References Cited

U.S. PATENT DOCUMENTS

| | | | |
|---|---|---|---|
| 3,878,230 | 4/1975 | Rothman | 260/410.9 N |
| 3,898,252 | 8/1975 | Serota et al. | 260/410.9 N |
| 4,091,005 | 5/1978 | Craig, Jr. et al. | 260/410.9 N |

*Primary Examiner*—Y. Harris-Smith
*Attorney, Agent, or Firm*—M. Howard Silverstein; William E. Scott; David G. McConnell

[57] ABSTRACT

Isopropenyl esters are prepared rapidly by reacting for about ten minutes at about 120° C. and a pressure of about 400 pounds per square inch a fatty acid and propyne in the presence of loaded zeolite catalyst.

9 Claims, No Drawings

RAPID PRODUCTION OF ISPROPENYL ESTERS

BACKGROUND OF THE INVENTION

1. Field of The Invention

This invention relates to a novel and rapid process for the preparation of isopropenyl esters.

2. Description of The Art

Known methods of preparing isopropenyl esters require reaction times of from two to twenty hours and higher reaction temperatures than that required in the process of the present invention. As described in U.S. Pat. No. 3,666,781, a reaction time of 4 to 16 hours at about 160° C. was required to make isopropenyl stearate. In addition, known procedures use catalysts that are homogeneous and soluble in the reaction mixture and consequently require process steps to remove the catalyst from the product.

SUMMARY OF THE INVENTION

An object of this invention is to provide a rapid method of preparing isopropenyl esters.

Another object of the invention is to provide a method of preparing isopropenyl esters in which the catalyst is heterogeneous and therefore insoluble in the reaction mixture.

A further object is to provide an essentially one step procedure for preparing isopropenyl esters.

A still further object is to provide a method of preparing isopropenyl esters which is easily adaptable to a large scale continuous reaction.

According to this invention the above objects are accomplished by a process wherein a fatty acid and methyl acetylene are reacted in the presence of ionic $Zn^{++}$ in the crystalline lattice of a loaded zeolite as a catalyst to produce a desired isopropenyl or diisopropenyl ester in high purity without having to remove zinc salt from the product.

DESCRIPTION OF THE INVENTION

The invention is useful for preparing the isopropenyl esters of the following types of compounds; normal and branched chain aliphatic acids, both saturated and unsaturated, having carbon chain lengths of from $C_2$ to $C_{22}$, saturated and unsaturated cyclic acids having carbon chain lengths of from $C_4$ to $C_{30}$ with and without normal and branched side chain substitution, aromatic acids, both mono and polycyclic, either singly or in various combinations of the aforementioned cyclic acids as a part of the aromatic molecule, acids other than carboxylic such as the sulfonic and phosphonic acids, either singly or in combination with any of the aforementioned structures to form a single molecule, a heterocyclic compound such as 2-ethyl pyridine and Koch acids having a total number of carbon atoms from $C_7$ to $C_{30}$, and fatty acids such as the mixture derived from saponified vegetable oils or the mixture derived from saponified animal oils and fats or any combination of these.

For the purpose of exemplifying this invention an extrudate of type Y zeolite was used. Other zeolites such as type X in powdered as well as extrudate form may also be used. Type Y has a composition of $Na_2O:Al_2O_3:3-6\ SiO_2$. When the $SiO_2:Al_2O_3$ molar ratio is 4.8, the hydrated unit cell composition is $Na_{56}[(AlO_2)_{56}(SiO_2)_{136}]\cdot264H_2O$. This crystallizes in the cubic system. An important building block of molecular seives of this type is the sodalite cage, a truncated octahedron unit consisting of $24(Si, AlO_4)$ units. This sodalite cage is connected through 4 of the 8 hexagonal faces in a tetrahedral arrangement to the surrounding sodalite cages. The pores thus created are defined by a 12-member ring of oxygen atoms, approximately 7-9 A° in size, opening into a central cavity of about 11 A° in diameter.

The zeolite was prepared in a conventional way using a 1N aqueous zinc acetate solution and drying the partially exchanged zeolite for about 16 hours at about 150° C. The dried zeolite contained about 4.0% zinc. Fifteen grams of the loaded zeolite plus 100 g (0.36 moles) of melted stearic acid were sealed in a 1-liter pressure vessel equipped with a magnetic stirrer, a gas inlet tube and a thermocouple, and the air within replaced by nitrogen. Approximately 80 ml of a liquified gas, the composition of which is about 60% of a 50—50 mixture of propyne and allene and about 40% propane, containing approximately 0.5 mole methyl acetylene in a pressure burette was pushed into the pressure vessel using pressurized nitrogen gas. An electric heater was used to heat the vigorously stirred mixture for 10 minutes at 120° C. at a pressure of about 400 pounds per square inch at which time the pressure vessel and its contents were rapidly cooled and the pressure in the vessel discharged to atmospheric pressure. Infrared analysis of the pale ivory colored solid gave the same spectra as that of a reference sample of isopropenyl stearate.

The process conditions are variable depending on the starting acid. The operable temperature is about from 100° C. to about 350° C., the actual temperature being consistent with the thermal stability of the particular starting acid. Pressures may also vary from about 50 pounds per square inch to about 500 pounds per square inch. The amount of loaded zeolite can vary from a few percent of the weight of the starting acid to about 25% of such weight. The amount of zinc loaded on the zeolite may range from about 0.4% to about 15%.

Loaded zeolites are usually dried at 500°-600° C. or higher. However, in the practice of this invention, I found that this was not necessary. In fact, I found that drying at about 150° C. for about six hours is advantageous in completing the reaction at a relatively low temperature in an unusually short period of time. Another advantage of this catalyst is, as previously noted, that it is insoluble in the product thereby eliminating any steps necessary to filter or distill the product to separate the product from the catalyst. The very short reaction time to obtain the desired product is completely unusual and unexpected.

The process of this invention is an excellent vehicle for large scale production of isopropenyl esters because it does not require the use of solvents or high temperatures, and does not require filtering or distillation equipment. The process is easily adaptable for continuous operation. The fatty acid and propyne are pumped under pressure through a heated, packed bed reactor of zinc loaded zeolite at an appropriate selected space velocity. Isopropenyl ester, free of zinc salt, is collected from the reactor. Purified propyne may be used or it may be a mixture of propyne and allene or it may be a mixture of about 60% of 50—50 mixture of methyl acetylene and allene and about 40% propane. In addition, allene may be used alone since under the conditions of the reaction, allene isomerizes to propyne.

I claim:

1. A process for preparing rapidly an isopropenyl ester comprising reacting a fatty acid with propyne in the presence of a loaded zeolite catalyst.

2. The process of claim 1 wherein the loaded zeolite catalyst contains about 4.0% zinc.

3. The process of claim 2 wherein the reaction is complete in ten minutes.

4. The process of claim 3 wherein the reaction is conducted at a temperature of about 120° C. and a pressure of about 400 pounds per square inch.

5. The process of claim 4 wherein the fatty acid has a carbon chain length of from $C_2$ to $C_{30}$.

6. A process for the rapid preparation of an isopropenyl ester comprising reacting at a temperature of from about 100° C. to about 350° C. and a pressure of from about 50 p.s.i. to about 500 p.s.i., a fatty acid with propyne in the presence of zeolite catalyst containing about 4.0% zinc, said fatty acid being selected from the group consisting of normal and branched chain aliphatic acids having a carbon chain length of from $C_2$ to $C_{22}$, saturated and unsaturated cyclic acids having carbon chain lengths of from $C_4$ to $C_{30}$, mono and polycyclic aromatic acids, sulfonic and phosphonic acids, heterocyclic compounds having carbon chain lengths of from $C_7$ to $C_{30}$, and fatty acid and mixtures thereof derived from saponified vegetable oils and from animal oils and fats.

7. A continuous process for preparing isopropenyl esters comprising pumping a fatty acid and propyne under pressure through a heated, packed bed reactor of zinc loaded zeolite at an appropriate selected space velocity and collecting the desired isopropenyl ester, from the reactor, said loaded zeolite containing from about 0.4% to about 15.0% zinc.

8. A process for preparing rapidly an isopropenyl ester comprising reacting for about ten minutes at a temperature of about 120° C. and a pressure of about 400 pounds per square inch, stearic acid with propyne in the presence of a loaded zeolite catalyst containing about 4.0% zinc.

9. A continuous process for preparing isopropenyl esters comprising pumping a fatty acid and propyne under a pressure of from about 50 p.s.i. to about 500 p.s.i. through a heated, packed bed reactor of zinc loaded zeolite at a temperature of from about 100° C. to about 350° C. at an appropriate selected space velocity and collecting the desired isopropenyl ester, from the reactor, said loaded zeolite containing about from 0.4% to about 15.0% zinc.

* * * * *